United States Patent [19]

Sanderson

[11] Patent Number: 4,704,404

[45] Date of Patent: Nov. 3, 1987

[54] PEROXYGEN-COMPOUNDS

[75] Inventor: William R. Sanderson, Warrington, England

[73] Assignee: Interox Chemicals Limited, London, England

[21] Appl. No.: 815,792

[22] Filed: Jan. 3, 1986

Related U.S. Application Data

[63] Continuation of Ser. No. 588,816, Mar. 12, 1984, abandoned.

[30] Foreign Application Priority Data

Mar. 15, 1983 [GB] United Kingdom ............... 8307036

[51] Int. Cl.$^4$ .................... A01N 37/16; C07C 179/24
[52] U.S. Cl. ...................................... 514/568; 252/95; 252/102; 260/502 R
[58] Field of Search ............. 260/502 R; 252/95, 102; 514/568

[56] References Cited

U.S. PATENT DOCUMENTS

| | | | |
|---|---|---|---|
| 2,058,315 | 10/1936 | Huttenlocher et al. | 260/502 R |
| 4,100,095 | 7/1978 | Hutchins et al. | 260/502 R |
| 4,154,695 | 5/1979 | McCrudden et al. | 252/94 |
| 4,278,615 | 7/1981 | Stober et al. | 260/502 R |
| 4,321,157 | 3/1982 | Harris et al. | 252/95 |

FOREIGN PATENT DOCUMENTS 1368400 9/1974 United Kingdom .

Primary Examiner—Howard T. Mars
Assistant Examiner—Bruce D. Gray
Attorney, Agent, or Firm—Larson and Taylor

[57] ABSTRACT

Increased energy costs have stimulated a demand for peroxygen compounds that are effective at ambient to hand-hot temperatures, but peroxyacids and acyl peroxides tend to suffer from one or more of poor thermal stability, or sensitivity to impact or moisture, thereby rendering their manufacture or storage hazardous, or from poor solubility. The instant invention provides salts of the formula (in anhydrous form):

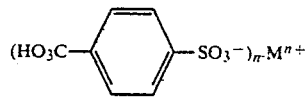

in which M represents potassium and n=1 or M represents magnesium and n=2. The solids can be incorporated in low temperature bleaching compositions, in washing compositions, in sanitizing compositions or in disinfection/sterilisation compositions.

7 Claims, No Drawings

PEROXYGEN-COMPOUNDS

This application is a continuation of application Ser. No. 588,816 filed Mar. 12, 1984, now abandoned.

The present invention relates to peroxygen compounds, and more particularly to salts of organic peroxyacids. The present invention also relates to compositions containing such salts, and the uses of such salts and compositions in cleaning, bleaching or disinfection.

For many years, it has been common for any washing or disinfecting compositions for the European market to contain a peroxygen compound, which can act as an oxidising agent, a bleach and to at least some extent a disinfectant. Particularly for washing or bleaching compositions, the peroxygen compound has typically been a particulate alkali metal persalt such as sodium perborate tetrahydrate or sodium percarbonate which generates hydrogen peroxide in aqueous solution. Similarly, in American, peroxygen compound-containing additives often in tablet form are widely available for use in conjunction with other washing compositions. Such persalts function most effectively at temperatures in excess of 80° C., but in recent years there has been a trend towards the use of synthetic fibres for apparel and household textile wares which may themselves or their finishes or dyes be adversely affected by exposure to high washing tempertures, and accordingly, increasing interest is being shown in washing at lower temperatures, for example in the range of ambient to 60° C. Interest has been further intesified by substantial increase in the cost of energy since the mid 1970's. For a peroxygen compound to be effective at such lower temperatures, it is necessary for it to be more active than the aforementioned persalts, and accordingly considerable research effort has been directed by many organizations to locate either more active peroxygen compounds or compounds which can be added to persalts in order to activate them. Both approaches suffer from their own disadvantages. The use of activators can be hindered by segregation of them from persalt during storage or transportation thereby leading to inconsistent washing performance, the need for both components to be dissolved simultaneously during the washing performance can lead to incomplete development of the active system during the restricted washing period available in most washing machines, and many can interact destructively with various other components in washing compositions. On the other hand, the more active peroxygen compounds are not without problems. First, many of them are comparatively unstable, even when stored alone, and this instability is compounded by formulation with the rest of the washing compositions, and many of such compounds are somewhat hazardous to handle, being sensitive to thermal shock, impact or other disturbance. In view of the problems associated with the existing active systems, there is a continuing need for alternatives having advantageous combinations of properties to be located.

In British Patent Specification No. 1368400, Procter and Gamble disclose bleaching compositions containing an organic peroxyacid having the generally formula $HCO_3-R-Y$, in which R is selected from, inter alia, arylene groups containing from 6 to 8 carbon atoms and Y is selected from, inter alia, groups providing in aqueous solution an anionic moiety attached to R, and water soluble salts of the organic peroxyacids. Examples of groups which provide an anionic moiety in aqueous solution include $-CO_2H$, $-CO_3H$, $-SO_3H$, and $SO_4H$. The aromatic nuclei of such peroxygen compounds can be substituted by any non-interfering substituent such as halogen groups. Although reference is made in generalised terms to the provision of water soluble salts of the organic peroxyacids, no such salts were actively tried and tested, and the only salts named were the sodium and potassium salts of diperazelaic acid and diperadipic acid as well as the monosodium salt of diperoxyterephthalic acid. Of these salts, no reference has been found in the literature to other than the sodium salt of diperoxyterephthalic acid, and even this salt was rated as very hazardous. Even if they could be isolated, the specified salts of diperazelaic and diperadipic acids would be exceedingly hazardous when measured by either the impact test, or the thermal stability test. Accordingly the said Procter and Gamble patent, and the many others by them that use the same or similar text in respect of organic peroxyacids and salts thereof, provide no functional teaching as to which salts of peroxyacids to use.

Many years ago, Huttenlocher and Lamatsch indicated in U.S. Pat. No. 2,058,315 the formation of various salts of aromatic persulphuric acids, including salts of toluene and napthalene persulphuric acids. Unfortunately, present day infra-red and chemical analyses show that the naphthalene-based salts are hydrogen peroxide adducts rather than peracids, so that the general teaching of this specification is open to doubt. Secondly, and perhaps more importantly, even though the toluene persulphonic acid salt appears to be a peracid salt, it lost at least 60% of its initial available oxygen in a week's storage, when its stability was measured under normal test conditions (30° C., a range of constant relative humidities at levels from 7 to 96%). Accordingly, this specification provides neither reliable teaching as to which peracid compounds can be formed nor as to the fitness of various peracid salts for incorporation in bleaching or detergent compositions.

Accordingly, it is an object of the present invention to provide in solid form salts which upon dissolution in aqueous media generate a peroxyacid and which do not require excessive desensitisation to enable them to be stored or transported. It is a further objective to provide bleaching, oxidising, or disinfecting compositions containing such salts, in some embodiments. It is a yet further object of other embodiments of the invention to provide processes for oxidising, bleaching or disinfecting, especially at ambient temperature to around 60° C. Other and additional objects of the present invention will be apparent from the detailed description of the invention below.

According to a first aspect of the present invention, there are provided in solid form, salts, expressed in anhydrous form, having the general formula:

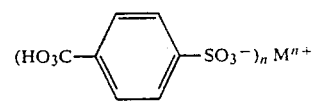

in which M represents potassium and n equal 1 or M represents magnesium and n equals 2.

It will be recognised that the salts specified in the first aspect of the present invention are a small selection from the many possible salts of substituted poeroxybenzoic acids for which theoretical structures could be proposed. First, it will be observed that the specified salts exclude the sodium salt even though the sodium salt of the 4-sulphoperoxybenzoic acid was obtainable. The hazard rating of the sodium salt, as measured by the standard drop weight test for impact sensitivity and as described herein subsequently, demonstrated that the salt was unduly hazardous and would require substantial desensitisation before it could be handled and transported with any assurance of safety. Secondly, it would be recognised that the selection is restricted to those salts in which salt is of the sulphonate group solely, in view of the difficulties of obtaining salts of peroxycarboxylic acid groups and the expected hazardous nature of them. Thirdly, the selection excludes any salts of 2-sulphoperoxybenzoic acid, by virtue of the very poor performance of such salts in use.

In a second aspect of the present invention, there is provided a process for the manufacture of the monopotassium salt or monomagnesium salt of 4-sulphopeoxybenzoic acid comprising the step of reacting a suspension of the corresponding salt of 4-sulphobenzoic acid in a strong acid with concentrated hydrogen peroxide until at least some of the carboxylic acid groups have been peroxidised at a temperature selected in the range of ambient temperature to 60° C., subsequently cooling the reaction mixture, and/or, augmenting the concentration of metal ions in solution by introduction thereinto of a soluble salt thereof to the extent necessary for a precipitate to form, and separating the precipitate from its mother liquor.

The corresponding salt from which the salt of the peroxyacid is made can readily be obtained by oxidation and partial neutralisation of 4-toluene sulphonic acid. A suitable method comprises refluxing the 4-toluene sulphonic acid in a moderately concentrated sodium hydroxide solution with, preferably, at least a stoichiometric amount of potassium permanganate for several hours and the remaining liquor then separated from precipitated manganese compounds. The filtrate can then be distilled, suitable under atmospheric pressure until about half the volume of liquor remained and upon cooling, for example to about 60° C. or lower, and acidification to mildly acidic, i.e. to a pH at or below the $pK_a$ of the carboxylic acid group and for safety's sake to about pH 3 whereupon the monopotassium salt of 4-sulphobenzoic acid precipitates out. Although a corresponding process could be effected with magnesium permanganate, such a reagent is not readily available and it is more convenient to obtain the magnesium salt by substitution of magnesium for potassium by dissolving the potassium salt in an aqueous solution of fluoroboric acid from which potassium fluoroborate precipitates and is filtered off and in to which resultant filtrate is stirred magnesium oxide, hydroxide or carbonate in a stoichiometric amount and which after evaporation yields a crystalline preceipitate of the monomagnesium salt of 4-sulphobenzoic acid. By making the potassium and magnesium salts in the aforementioned way, the starting material is in a suitable form, in respect of its particle size distribution for use in a subsequent peroxidation reaction.

The strong acid employed in the peroxidation reaction is typically methane sulphonic acid, or any acid having approximately comparable or even higher acid strength. Such alternative acids include sulphuric acid or a mixture thereof with methane sulphonic acid and optionally the strong acid reaction medium can comprise or include phosphoric acid. The concentrated hydrogen peroxide is typically employed in a concentration of at least 60 and generally at least 70% w/w and preferably in a mole ratio to the non-peroxygenated salt of at least 1 mole per mole of the latter. It would be recognised that there are various ways that are suitable for bringing the solid salt into contact with the hydrogen peroxide. The hydrogen peroxide can be introduced gradually into a body of the suspension of salt in the strong acid, or the solid salt into a solution of the hydrogen peroxide, or they can be introduced simulteneously or alternately into a body of the reaction mixture, and after a suitable reaction period the solid product is separated from the mother liquor. Alternatively, the two reagents can be introduced in regulated fashion into the body of the reaction mixture either continuously or intermittently and when the reagents have been introduced in an appropriate mole ratio a proportion of the body can be withdrawn continuously or intermittently as desired for product recovery therefrom. The rate of introduction of the reagents and rate of removal of reaction mixture from the body is desirably balanced so as to provide a residence time within the range given hereinafter. In other variations, the mother liquor from which product has been removed can be recycled and this can be employed in whole or in part as the process operator so desires, together with any fresh solvent, hydrogen peroxide and non-peroxygenated salt needed to sustain the cycle. Many variations in the manner of introduction of the reagents, solvent and any recycled mother liquor into the reaction vessel can be made. Examples include the premixing of all or part of one reagent, e.g. the non peroxygenated salt, with recycle mother liquor and/or fresh solvent, premixing all or part of the other reagent with the other of the mother liquor or fresh solvent, and at the other extreme is the separate and simulteneous or phased introduction of all of the reagents, solvent and any recycled mother liquor. Intermediate variations are permissible also. It will be recognised that such variations are within the capability of practising Chemical Engineers, and require no further clarification.

The mole ratio of hydrogen peroxide to non-peroxygenated sulphobenzoic acid salts is generally selected in the range of from 1:1 to 10:1 and in many embodiments from 1.2:1 to 5:1. Naturally, any residual hydrogen peroxide in the mother liquor after separation from the peroxygenated salt is normally taken into account in determining the amount of fresh hydrogen peroxide that should be added to restore its concentraton to its original level for reaction with further non-peroxygenated salt. Such residual hydrogen peroxide can often be obtained by employing an initial mole ratio of at least 2:1.

Conveniently, there is no need for the reaction to be carried out at a temperature in excess of about 60° C. and it is preferred on general safety grounds to operate at a temperature of not above 50° C. Naturally, the reaction period, or the corresponding residence time in a continuous process, is increased at lower reaction temperatures in order to ensure that a given proportion of the salt is peroxygenated. For convenience it is preferred not to exceed a reaction period/residence time of 10 hours and in fact the reaction temperature is within the region of 30° C. to 45° C., so that a reaction period/residence time selected within the range of half an hour to 4 hours enables substantially complete peroxygenation to occur.

The resultant peroxygenated salt has been found to be very soluble in aqueous media, and accordingly its isolation from the reaction mixture is markedly assisted by the step of enforced cooling, preferably reducing the temperature of the reaction mixture by at least 15° C. and alternatively or additionally by the introduction of a more soluble potassium or magnesium salt into solution. An especially convenient example of such a soluble potassium or magnesium salt is the sulphate or nitrate. One particularly convenient form in which to introduce it is as a substantially saturated solution in water, and preferably chilled water but introduction as a suspension or even in particulate form can be contemplated alternatively. The salt of the 4-sulphoperoxybenzoic acid precepitates from the reaction mixture and this preceipitate can subsequently be washed, preferably with a saturated potassium or magnesium sulphate solution as corresponds to the persalt.

Hereinafter, the potassium and magnesium salts of 4-sulphoperoxybenzoic acid may be referred to as respectivley KSPB and MSPB. The impact sensitivity of the potassium and magnesium salts is markedly less than that of the corresponding sodium salt, each being made by the same manufacturing route outlined herein before. The sodium salt had $E_{50}$ figure of about 10 kg/cm whereas the magnesium salt had an $E_{50}$ of 66 kg/cm and the potassium salt had an $E_{50}$ from various examples that usually ranged from about 100 kg/cm to over 500 kg/cm. From these figures it can be seen that the impact sensitivity of salts of sulphoperoxybenzoic acids could not be predicted in advance, in that all three would be expected to have very similar impact sensitivities yet the figures range from the sodium salt which is so impact sensitive that even manufacture on a commercial scale would be hazardous let along its subsequent handling or transportation, through the magnesium salt which is to some extent impact sensitive but which can readily be desensitised, to the potassium salt which ranges from being readily densensitisable through to being not sensitive. The impact sensitivities were measured by the standard drop weight test as described in European Patent Specification No. 27693 lines 2 to 32, page 12 incorporated by reference herein.

Of considerable importance for a peroxygen compound is its thermal stability. As a general rule peroxyacids have poor stability, e.g. monoperoxysuccinic acid has an S.A.D.T. of only 38°/40° C. and diperoxydodecanedioic acid similarly, when calculated at the 25 kg container scale, thereby rendering summer storage of such compositions undesirable. However, the invention compounds are well above this range, and KSPB demonstrates a remarkable stability in that it yields no exotherm at up to 140° C. so that the SADT is well in excess of 100° C.

Where it is desired to desensitise the KSPB or MSPB, this can readily be effected by bringing the salts into intimate contact with a desensitising amount of a diluent, such an amount normally being at least half the weight of KSPB and normally at least the weight of MSPB. Once the salt has been desensitised, any further diluent is at the discretion of the formulator. It is usual for the desensitised composition to have an avox of at least 0.5% w/w which corresponds to a minimum KSPB or MSPB content in the desensitised composition of 7%, approximately, and in practice it is often preferable for the concentration of the salt to be selected within the range of 10 to 70% w/w for KSPB and 10 to 50% for MSPB.

One class of desensitising diluents comprises alkali metal or alkaline earth metal salts of halogen-free acids and especially of strong acids. In particular such diluent salt, are often sodium, potassium, or magnesium salts especially of sulphate compound by sulphate or mixtures thereof ortho, pyro or polyphosphates or mixtures thereof organic acids including $C_8$ to $C_{20}$ mono basic or dibasic acids and aromatic acids in which the benzene nucleus is subsituted by at least one carboxylic acid group and if desired one or more lower alkyl such as methyl, or sulphonate groups. Additionally, all or part of the aliphatic or aromatic acids can be present in acidic form in so far as they are solid in use.

Other suitable inorganic diluents include boric acid and alkaline earth metal borates, solid aluminum salts sodium carbonate and/or bicarbonate including natural or synthetic zeolites and clays, and various hydrogen peroxide-developing persalts such as sodium perborate or sodium percarbonate.

Other organic diluents include hydrocarbon waxes, C1–C6 esters of aromatic acids especially of phthalic acid and solid dextrins, gelatines and starches. The KSPB and/or MSPB can be diluted using various techniques such as simply admixture, possibly followed by tabletting or enclosure within a pouch or other enclosure which either ruptures or is penetrated in use, or is removed, or ruptured before use by the user. Other suitable techniques include agglomeration, granulation, pelletisation, formation of extrudates or noodles or alternatively accommodation of 2 or more of the foregoing techniques. Alternatively or additionally, at least part of the diluent may comprise a film-forming substance such as aliphatic fatty acid amides or esters, fatty alcohol polyglycol ethers, polyethylene glycol or fatty acid or amide derivatives thereof, and esters and amides of polyols such as glycerol or sorbitol and ethoxylated derivatives. Such coatings can perform the dual function of dilution and isolating the peroxyacid from other components of compositions with which it may be mixed subsequently, and of course preformed granulates, agglomerates, or extrudates containing either the particulte KSPB or MSPB alone or with one or more of the non-film forming diluents can also be coated.

It will be recognised that various of the aforementioned diluents are valued components in their own right of washing compositions or bleaching compositions or disinfectant compositions, for example, those compounds which act either as builders or as regulators or those salts which can lose water of hydration, or boric acid are exotherm control agents. It will therefore be recognised that the incorporation of such dual or even triple function diluents in the composition in the appropriate amounts can lead to the generation of aqueous solutions either of the composition by itself or in the presence of some other compositions such as a washing composition having a pH within a wide range from mildly acidic through neutral to moderately alkaline by the use of respectively acids and bases or alkaline buffers in varying ratios with each other and with the KSPB or MSPB. Naturally, the higher proportion of acids such as boric acid or organic acids or zeolites in acid form tend to produce less alkaline solutions whereas bases like sodium carbonate and buffers like the various sodium phosphates which produce more alkaline solutions. Test results confirm accepted wisdom that optimum bleaching occurs around the $pK_a$ for the peroxyacid, i.e. in the region of pH 8 +/−0.5 pH units, and that its effectiveness progressively increases from a pH such as 10 through 9 to 8. Consequently according to a further aspect of the present invention there are provided particulate compositions comprising at least 10% w/w KSPB or MSPB together with 1 or more solid pH regulators selected from inorganic acids or organic acids and one or more builders or buffers selected from alkaline phosphates, carbonates, silicates, borates amino carboxylates or phosphonates present in a total amount of at least 50% of the composition and in such relative amounts that the pH of a 1% solution in the range of from 7 to 8.5. Such compositions can readily be employed for washing, bleaching or disinfecting absorbent materials, hard surfaces, and aqueous media. Compositions directed more to disinfection are preferably buffered to provide pH 5 to 8.

The aforementioned compositions can be employed by themselves, or they can be employed in conjunction with surfactant-containing compositions or can be incorporated within such compositions. The nature of such other compositions will vary to some extent depending on the intended primary purpose of such compositions. Such compositions can be classified as general household washing compositions or sanitising/disinfecting compositions. General household washing compositions often contain at least 1% and in many cases from 5 to 95% and particularly from 5 to 40% by weight of one or more anionic, cationic, nonionic, zwitterionic, amphoteric or ampholytic surfactants, and in addition generally contain one or more builders in an amount from 1 to 90% and frequently from 5 to 70% by weight of the compositions, especially in a weight ratio to the surfactant of from 1:2 to 10:1. Such household washing compositions optionally can contain up to 40% by weight of a processing aid such as sodium or magnesium sulphate and optionally one or more auxilliary agents, often up to a total amount of not more than 20% of the composition, such as soil anti-redeposition agents, dye transfer inhibitors, optical brightening agents, peroxygen stabilisers, corrosion inhibitors, bactericides, dyes, perfumes, foam enhancers, foam inhibitors, pH regulators, adsorbents, and abrasives. Such washing compositions tend to be employed in a weight ratio to the aforementioned KSPB/MSPB bleaching or sanitising compositions of 5:1 to 1:5. When the bleaching or sanitising compositions are incorporated within the washing composition, KSPB and/or MSPB are present in the total composition of not more than 40% and in many cases at least 0.5%. In general, by virtue of their activity, they are often present in an amount of not more than 10% w/w.

Representative surfactants can include soaps, alkyl benzene sulphonates, olefin sulphonates, linear alkane sulphonates, hydroxy-alkane sulphonates, alcohol sulphates, alkyl phenyl-ethylene oxide ether sulphates, tetra alkyl ammonium halides or alkyl pyridinium halides, condensed polyethylene oxide alkyl phenols or naphthols, fatty acid esters of polyols, polyglycols, amine oxides, phosphine oxides and suitably selected sulphonium and phosphonium amphoteric surfactants containing an anionic water-solubilising group.

It will readily be understood that the aforementioned organic complexing agents can fulfil useful functions even when they are incorporated at low levels of, for example 0.1 to 5% w/w of the composition, i.e. at levels below the normally encountered builder levels. By so doing, the stability of the peroxygen compounds can be improved in use, and this can result in more efficient or improved bleaching. Many of such complexing agents satisfy the general formula:

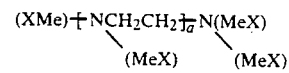

in which X represents a carboxylic acid or especially a phosphonic acid group or an alkali or alkaline earth metal salt thereof, such as sodium, potassium, calcium or magnesium salt or an ammonium salt and a represents either 0, 1 or 2, including EDTA, EDTMP, DTPA and DTPMP.

Various of the suitable builders have been specified hereinbefore in conjunction with the bleach/sanitising composition. Amongst organic builders which are suitable herein as well as in the aforementioned bleaching compositions, which generally fall within the classes of alkaline salts of hydroxycarboxylic acids, polycarboxylic acids, amino polycarboxylic acids and polyphosphonic acids, particular mention should be accorded to sodium citrate, sodium salt of nitrilotriacetic acid and oxydisuccinic acid.

Amongst the auxiliary agents, sodium carboxymethylcellulose is of particular value as a soil antiredeposition agent and derivatives of diaminostilbene sulphonic acid and 1,3-diaryl-2-pyrazolines and aminocoumarins are typical optical brighteners. Proteolytic enzymes, if incorporated, are preferably coated with for example a non-ionic surfactant so as to minimise interaction with the peroxyacid salt. Amongst peroxyacid stabilisers there can be included such compounds as 8-hydroxy quinoline.

Any of the aforementioned invention washing composition can also contain if desired one or more inorganic persalts such as sodium perborate monohydrate or tetrahydrate or sodium percarbonate. Such persalts are often present in peroxyacid-free washing compositions up to 40% thereof, and when the KSPB and/or MSPB is incorporated, they can conveniently be present in a weight ratio of up to 5:1 thereto, the total of persalts and salt of peroxyacid preferably reaching no more than 40% of total composition. Compositions containing the persalt/peroxyacid mixture particularly benefit from incorporation of the low levels of especially amino phosphonic acid complexing agents, as referred to herein.

When considering sanitising/disinfecting compositions, it is common for the peroxyacid compositions to incorporate some additional component such as an alkali metal chloride or bromide, which in many cases comprises up to 70% of the total composition. Accordingly, such sanitising compositions can be regarded as a mixture of the aforementioned washing compositions containing peroxyacid with, in many cases, from 0.5 to 2 parts by weight of alkali metal chloride or bromide. In practice this leads to compositions comprising up to 40% of KSPB or MSPB, from 1 to 70% alkali metal chloride or bromide, from 0 to 50% of the surfactant, and from 0 to 70% of the builder. Within such formulations, KSPB or MSPB is preferably present in an amount from 5 to 20%, the alkali metal chloride or bromide is preferably present in an amount of at least 30%, the total builder including acidic component is preferably at least 10 to 50% and in practice often comprises from 5 to 30% of a phosphate builder and from 5 to 30% of a non-phosphate builder such as sodium carbonate or bicarbonate. Such compositions are particularly suited for the cleansing and sanitising of absorbent materials such as terry that has been soiled with human or animal waste products, especially from babies. One of more of the aforementioned auxilliary agents, generally in an amount of 5 to 20% of a total composition, as before, can likewise be included.

In practice, KSPB and MSPB are obtained in particulate form, and they can be subsequently sieved, granulated, agglomerated or otherwise aggregated as necessary in order to produce particles generally within the range of 0.01 mm to 2 mm and especially from 0.05 mm to 1 mm, thereby to match to a reasonable extet the particle size ranges of other components in the compositions of which they are the peroxyacid-generating components. By so doing, it is possible to minimise problems of segregation which could otherwise arise during transportation and handling of the product.

The processes for washing articles according to the present invention can be carried out at a temperature from ambient temperature up to the boiling point of the washing solution. Compositions according to the present invention are particularly well suited to a process at which washing or bleaching is carried out by steeping at ambient or by heating the solution to a temperature from about 25° to 60°. Alternatively the washing and bleaching processes may be effected by heating up a cold washing solution. A combination of processes can be used, such as cold steeping followed by a wash at 30, 40 or 50° C. By virtue of the very rapid rate of dissolution of KSPB and MSPB in aqueous solution even at low wash temperatures, compositions, containing suchy bleaching agents are particularly suitable for use at temperatures in the range of ambient temperature to 40° C., ambient often being regarded as about 25° C. Incorporation of an inorganic persalt, such as sodium perborate or percarbonate into KSPB/MSPB washing compositions imparts improved higher temperature wash capabilities so that the solution can be heated with advantage to hot wash conditions, i.e. often 80° to 90° C.

In general, it is desirable for washing or bleaching solutions for use in the home to contain at least 1 part per million Avox. Household washing solutions prepared by dissolution of detergent compositions in general provide no more than about 200 ppm. Avox., frequently no more than 100 ppm Avox, and often at least 10 ppm Avox.

In general, the rate of removal of stains is enhanced by employing a higher temperature and by higher Avox. concentrations, but by virtue of the rapid rate at which KSPB and MSPB dissolve in water or aqueous detergent solutions, the contact period between solution and fabric can conveniently be as short as 5 minutes. Longer periods of for example, up to 1 hour tend to provide greater soil removal. In cold washing or steeping even longer periods can be employed, such as steeping overnight.

Many washing compositions are formulated so as to extract stains from fabrics into solution and to minimise the redeposition of such stains or dye transfer onto the fabric. Consequently, it is extremely desirable for the bleaching agent to be able to bleach stains in solution, and in this respect KSPB and MSPB are particularly useful on account of their comparatively high rate of solubility in aqueous alkaline solutions, thereby enabling the peroxyacidic species to be present in solution when the stains are extracted. However, even though KSPB and MSPB provide a more active bleaching species, damage to the dyestuffs in coloured fabrics is comparable with that caused by inorganic peroxygen compounds employed heretofore, and thus enables washing compositions containing KSPB and MSPB to be employed for coloured fabrics as well as for whites.

It will be fully recognized that the amount of washing composition containing KSPB or MSPB, to employ in order to achieve such concentrations of Avox in the final solution is a function of the proportion of that percompound in either the washing composition or the bleaching composition employed in conjunction with some other washing composition. In practice, though, it is usual for the amount of percompound-containing washing composition to be employed at a concentration of from 0.5 gpl to 10 gpl and often from 0.8 gpl to 5 gpl, washing practices varying from country to country. When the bleach composition is used as an additive in conjunction with the washing composition or introduced separately into for example a subsequent rinsing stage, it is often employed at a concentration of from 0.3 to 4 gpl and in many instances from 0.5 to 2.5 gpl. Use outside these ranges is, of course, at the discretion of the user.

The sanitiser compositions are often employed in dilute aqueous solution and concentration of from 1 to 20 gpl. Fresh or replacement solution is often prepared at hand hot temperatures, typically 35° to 45° C., or higher temperatures could be employed if desired and thereafter either heated continuously or intermittently so as to maintain an elevated temperature or allowed to cool to ambient temperature whilst the solution is in contact with the articles to be sanitised. The solution can be partially or completely replaced periodically, commonly on a daily basis, and at the discretion of the user, the concentration of the sanitiser composition in solution can be augmented from time to time so as to restore the peroxyacid concentration to its former level. The articles to be sanitised are normally allowed to remain in solution for a considerable period of time, generally at least 4 hours and in many cases overnight or longer. If desired, the articles can be dried and reused or subjected to an interposed normal washing process.

In processes for the disinfection/sanitising of aqueous media, such as recirculating water systems, such as in industrial cooling circuits, or effluents from food-processing industries, paper mills, sewage stations, or in potable or industrial water supplies, optionally chlorinated, the disinfection process can conveniently be effected by introducing the KSPB/MSPB together with any pH regulator or buffer as desired into the aqueous media particularly into employ pH generally in the region of from 5 to 9, and in general, sufficient of the salt is added to provide a concentration of at least 1 ppm KSPB/MSPB in the media often from 1 to 25 ppm. Use of the composition in such concentrations leads to a substantial reduction in the content of live microorganisms. In the event that the aqueous media contain oxidisable waste chemicals such as inorganic or organic cyanides and mercaptans and the like, at least one mole of KSPB/MSPB should be employed per mole of oxidisable substance. The pH of such media is preferably adjusted beforehand to and maintained at the known pH safe peroxyacid reaction with such substances, e.g. above pH 9 for cyanides.

In addition to washing and/or bleaching fabrics, the compositions can be used to clean hard surfaces such as metal, plastic or wooden surfaces, either by dissolving washing or bleaching compositions in water, preferably to provide 200 ppm to 2000 ppm avox especially 400 to 1000 ppm avox or by forming a slurry or paste of such compositions. Also, if desired, solutions produced by the dissolution of compositions described herein can be used to bleach textile fabrics, wood or pulp under the conditions, and employing the equipment used for bleaching such articles with hydrogen peroxide or inorganic peroxoacids.

Having described the invention in general terms, specific embodiments will be described more fully by way of example. Modifications to the following can be made by the skilled artisan without departing from the spirit of the invention.

EXAMPLES 1 AND 2

Preparation of Starting Materials

The potassium salt of 4-sulphobenzoic acid was prepared in the following manner. A solution of potassium permanganate (480 g in 8.5 l of water) was introduced gradually over an 8 hour period into a boiling solution of 4-toluene sulphonic acid (360 g) dissolved in a solution of sodium hydroxide (200 g, 100° Tw. in 2 l of water). The mixture was then boiled under reflux for a further 12 hours during which approximately 6 liters of liquid distilled off. The resultant concentrated reaction liquor was then filtered to remove therefrom precipitated manganese compounds and combined with the result of two repetitions of the process. The resultant liquor was then further distilled under atmospheric pressure to remove therefrom about 9 liters of distillate and the boiler liquor, after being cooled to 60° C. and acidified to pH 3 by addition of concentrated hydrochloric acid (1 kg) yielded a crystalline precipitate. Further precipitate occurred upon further cooling and evaporation. The precipitate was then washed with ice/water (50 ml) and oven dried at 100° C. to yield colourless prisms of 4-sulphobenzoic acid-potassium salt (yield, 0.5 kg, melting point above 300° C.).

The corresponding magnesium salt was obtained by substituting magnesium or potassium in a process in which fluoroboric acid (3.5 g, 50% active) was introduced into a solution of the potassium salt (17.3 g) in water (450 ml) and the mixture stirred for 10 minutes. The precipitate, potassium fluoroborate, was filtered off and magnesium oxide (1.7 g, 99% purity) was introduced into the filtrate with agitation. The resultant clear solution was then evaporated under reduced pressure to a low volume whereupon a white solid crystallised out which after separation by filtration and drying at 35° C. yielded 4-sulphobenzoic acid-magnesium salt (5.9 g, magnesium content 5.35%). The theoretical magnesium content would have been 5.63%.

Preparation of KSPB—(Example 1.)

4-sulphobenzoic acid - potassium salt (10.4 g) was suspended in methane sulphonic acid (72.4 g) at 40° C. an aqueous hydrogen peroxide (7.2 g ; 85% w/w) was slowly introduced and the reaction mixture was stirred continuously at 40° C. for a total of 3 hours. The reaction mixture was then cooled by introduction of crushed ice (50 g) and a saturated solution of potassium sulphate (75 ml of solution at ambient temperature) was then introduced, resulting in the precipitation of a solid. The precipitate was filtered off, washed twice with solutions of saturated potassium sulphate (75 ml and 50 ml respectively), dried under suction, and finally dried under vacuum over phosphorus pentoxide. The resultant crystalline product was obtained in a yield of 9.2 g and had an Avox content of 5.7% as O measured by the standard determination using potassium iodide and titration of the liberated iodine using sodium thiosulphate.

The theoretical yield would have been 11.1 g and theoretical Avox 6.25%. The potassium content was 14.6% (theoretical value 15.2%) and examination of the infrared spectrum revealed peaks at 1750 cm$^{-1}$ and between 1150 and 1250 cm$^{-1}$ but only a minor peak at 1700 cm$^{-1}$ demonstrating the existence of the percarboxylic acid and sulphonate groups and a minor amount of carboxylic acid groups respectively.

Preparation of MSPB—(Example 2.)

4-sulphobenzoic acid-magnesium salt (25.8 g) was suspended at 40° C. in methanesulphonic acid (180 g) and aqueous hydrogen peroxide (17.9 g, 85% w/w) was slowly introduced therein with stirring. The reaction mixture was stirred at 40° C. for a reaction period of 3 hours, whereupon it was cooled, crushed ice (200 g) was added and then a saturated solution of magnesium sulphate (150 ml) was introduced. A product precipitated out, filtered off, washed twice with further amounts of saturated magnesium sulphate (30 ml and 20 ml) and finally washed twice with ethanol (30 ml, 30 ml) under partial vacuum. The yield of product after drying under vacuum over phosphorus pentoxide was 16.5 g, and the product had an Avox of 5.2% as O, determined as before. The theoretical yield was 27.7 g and theoretical Avox 7.0%. The magnesium content of the sample was 5.33% compared with a theoretical content of 5.24% and an infra-red spectra showed peaks at 1750 cm$^{-1}$, 1100 to 1250 cm$^{-1}$ and a small peak at 1700 cm$^{-1}$, which demonstrated the existence of the percarboxylic acid, sulphonate groups and a minor amount of carboxylic groups respectively.

Testing of the products

The impact sensitivities of KSPB and MSPB were measured using the standard impact sensitivity test to which reference has been made hereinbefore and the description given in European Patent Specification No. 27693 in the name of Interox Chemicals Limited. The $E_{50}$ figure for KSPB made hereinabove is about 500 kg-cm but certain other samples when prepared by the corresponding route had an $E_{50}$ of about 100 kg-cm. This demonstrates that KSPB ranges from being completely non-hazardous to impact sensitivity to being only slightly hazardous and very readily desensitised. The $E_{50}$ for MSPB, measured by the same test, was 66 kg-cm indicating that the product as made was somewhat impact sensitive but that it was possible for it to be desensitised by the techniques described hereinbefore.

By way of comparison, the corresponding sodium salt, made in an analogous manner to MSPB and having an Avox of 4.86% as O in comparison with a theoretical Avox of 6.67%, had an $E_{50}$ figure of below 10 kg-cm in the same test.

The storage stability of KSPB and MSPB was measured by small weighed amounts of the respective salt having known Avox content of respectively 5.25% and 5.2% in containers having a measured relative humidity. The containers were then stored for a week at 30° C. and the Avox of each sample redetermined. The results are summarised in the foregoing table below.

| % relative humidity | KSPB % Avox | MSPB % Avox |
|---|---|---|
| 7 | 4.82 | 5.10 |
| 12 | 4.88 | 6.10 |
| 22 | 4.85 | 5.24 |

-continued

| % relative humidity | KSPB % Avox | MSPB % Avox |
|---|---|---|
| 33 | 4.91 | 5.38 |
| 43 | 4.91 | 5.43 |
| 52 | 4.98 | 4.75 |
| 63 | 4.90 | 4.90 |
| 75 | 4.88 | 5.23 |
| 84 | 3.48 | 4.73 |
| 96 | 5.08 | 4.80 |

From Table 1 it can be seen that both KSPB and MSPB were not only relatively stable salts, and much better than organic peroxyacids and salts thereof, in general, but also that the stability was substantially insensitive to the relative humidity of the environment which is of special practical importance in that fluctuation in relative humidity can be tolerated readily.

In a further demonstration of the stability of the particular salts, a further sample of KSPB was stored in a container at 30° C. The Avox of the product was measured periodically. It had fallen from 5.39% to 4.84 after 1 week's storage and to 4.70% after 18 weeks' storage, a total reduction of only 13%, most of which occurred in the first week of storage. This demonstrates the extremely and surprisingly good stability of the product.

Compositions containing KSPB/MSPB Biocidal Formulations

| Components | BO1 % w/w | | BO2 % w/w |
|---|---|---|---|
| KSPB (5.25% Avox) | 11.2 | KSPB | 12 |
| LAS | 7.0 | LAS | 7 |
| Boric Acid | 5.0 | Sodium carbonate | 23 |
| NaH$_2$PO$_4$ | 10.0 | Sodium tripolyphosphate | 10 |
| Corrosion Inhibitor | 1.0 | | |
| Perfume | 0.5 | Sodium chloride | 48 |
| Na$_2$SO$_4$ | 65.3 | | |

Dosage of 1 gpl of the formulation BO1 would provide about 6 ppm Avox. and 4 gpl of BO2 about 25 ppm Avox.

Bleaching Formulations

| Components | BL1 % w/w | BL2 % w/w | BL3 % w/w |
|---|---|---|---|
| KSPB (5.25% Avox) | 7.6 | 30.5 | 61.0 |
| Surfactant | 4.0 | 4.0 | 4.0 |
| Optical Brightening Agent | 0.1 | 0.1 | 0.1 |
| Boric acid | 10.0 | 10.0 | 10.0 |
| Sodium Sulphate | 78.3 | 55.4 | 24.9 |

Dosage of the formulations at 1.25 gpl would provide respectively 5 ppm, 20 ppm and 40 ppm Avox.

Washing Formulations

| Components | DB1 % w/w | DB2 % w/w | DB3 % w/w |
|---|---|---|---|
| KSPB | 6.3 | 11.1 | 15.9 |
| Boric Acid | 10.0 | 10.0 | 10.0 |
| Sodium tripolyphosphate | 29.5 | 24.7 | 19.9 |
| Na$_2$SO$_4$ | 14.0 | 14.0 | 14.0 |
| Na$_2$SiO$_3$ | 14.0 | 14.0 | 14.0 |
| LAS | 7.0 | 7.0 | 7.0 |
| Non-ionic surfactant | 5.1 | 5.1 | 5.1 |
| Soap | 6.4 | 6.4 | 6.4 |
| EDTA | 0.13 | 0.13 | 0.13 |
| CMC | 1.0 | 1.0 | 1.0 |
| Optical Brightener | 0.13 | 0.13 | 0.13 |
| Water | | balance | |

Washing Formulations

| Components | DB4 % w/w | DB5 % w/w | DB6 % w/w |
|---|---|---|---|
| LAS (C11.5) | 7.0 | 6.0 | 6.0 |
| Tallow alcohol ethoxylate (14EO) | 2.5 | 6.0 | 7.0 |
| Sodium Soap (C18) | 3.0 | 3.0 | 2.0 |
| Sodium tripolyphosphate | 40.0 | 30.0 | 30.0 |
| Sodium silicate | 6.5 | 5.0 | 5.0 |
| Magnesium silicate | 1.5 | — | — |
| Boric acid | — | 6.0 | 8.5 |
| CMC | 1.0 | 1.0 | 1.0 |
| EDTA-Na$_2$ | 0.2 | — | 0.2 |
| EDTMP-Na$_4$ | 0.2 | — | — |
| OBA | 0.2 | 0.2 | 0.2 |
| Na$_2$SO$_4$ | 18.5 | 23.5 | 16.0 |
| KSPB | 11.0 | 11.0 | 7.0 |
| PBS monohydrate | — | — | 9.0 |
| Perfume | 0.1 | 0.1 | 0.1 |
| Water (bound) | | balance | |

Compositions having substantially similar properties are obtained by replacing all or part of the KSPB with MSPB, except for BL3.

Performance

The washing performances of KSPB and MSPB were tested by washing swatches of cotton cloth, which had been prestained with red wine, at 40° C. for 10 minutes and 20 minutes respectively using an aqueous solution of a detergent composition (4 gpl) which analysed as follows:

| % w/w | |
|---|---|
| 45.8 | STPP (Na$_5$P$_3$O$_{10}$) |
| 14.0 | Na$_2$SO$_4$ |
| 14.0 | Na$_2$SiO$_3$ |
| 7.0 | L.A.S (Linear alkyl benzene sulphonate) |
| 5.1 | Non-ionic surfactant |
| 6.4 | Soap |
| 0.13 | EDTA |
| 1.0 | C.M.C (Carboxymethyl cellulose) |
| 0.13 | Optical brightening agent |
| balance | H$_2$O |

The water had a hardness of 250 ppm, in a calcium/magnesium weight ratio of 3:1. The KSPB and MSPB provided an Avox in solution of 35 ppm and for comparison, results are given also for a widely recognised bleach activator system under the same conditions, namely tetraacetylethylenediamine/sodium perborate tetrahydrate in a 1:1 mole ratio and 35 ppm Avox.

The trials were carried out in a laboratory scale washing machine sold under the name TERGOTOMETER (Trade Mark) by the U.S. Testing Corporation which simulates the action of a vertical agitator type domestic washing machine. After being washed, each swatch was rinsed with cold water and hot air dried. The reflectance of each swatch was determined after washing ($R_f$) and compared with its pre-washed reflectance ($R_i$) and that of the unstained cloth ($R_u$) giving a measure of stain removal, using an instrumental colour system MICROMATCH reflectance spectrophotometer equipped with a xenon light lamp light source and a D65 filter to approximate to CIE artificial daylight. An average of 4 reflectance readings were taken for each swatch backed by three thicknesses of unstained material. The percentage stain removal was obtained using the formula percentage:

$$\% \text{ stain removal} = 100 \times (R_f - R_i)/(R_u - R_i).$$

The results are summarised in Table 3 below.

TABLE 3

| Bleach Agent | pH | % Stain Removal 10 Mins | 20 Mins |
| --- | --- | --- | --- |
| TAED/PBS | 8 | 51.9 | 71.3 |
| KSPB | 8 | 76.3 | 85.3 |
| MSPB | 8 | 72.0 | 82.7 |
| TAED/PBS | 9 | 62.0 | 74.0 |
| KSPB | 9 | 52.1 | 61.3 |
| MSPB | 9 | 46.7 | 61.1 |

From Table 3 above, it will be recognised that both KSPB and MSPB are sensitive to changes in pH and that at or near pH 8, they are markedly superior to the widely accepted activator system.

By way of comparison, when the corresponding washing trials were carried out using the magnesium salt of the 2-sulphoperoxybenzoic acid, under identical conditions, o there was no substantial soil removal attributable to the peroxyacid at all, removals at pH 8 or 9 being substantially the same as in its absence, and not exceeding 30% even after 20 minutes. These results, therefore, demonstrate clearly the markedly better performance of the 4-sulphoperoxybenzoic acid salts in comparison with the 2-sulphoperoxybenzoic acid salts.

DISINFECTION

The effectiveness of KSPB as a microbiocide can be judged from the following test.

1ml of a mixture of spores and vegetative cells from a 10 day culture of *Bacillus subtilis* NCTC 10452 grown in a sporulation broth containing 10 g peptone $1^{-1}$ and 20 mg manganese (II) sulphate $1^{-1}$ was shaken on a vortex mixer, with glass balls in the tube assisting the disintegration of the pellicles before being added to 100 ml of a freshly-made solution of KSPB (0.05% w/w). After 24 hours exposure at ambient temperature, the bacteria were collected on a Millipore filter (porosity 0.45 μm), rinsed with sterile quarter-strength Ringer solution and then incubated on membrane plate count agar for 48 hours at 37°. Fewer than twenty colonies were present on the filter. Such a number can arise from the carry over from previous samples. The test can consequently be considered successful in that the reduction in the number of live bacteria was from $1.2 \times 10^7$ to below 20.

I claim:

1. A compound in solid, anhydrous form of the formula:

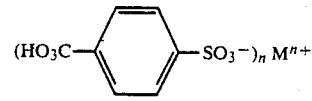

in which M represents potassium and n equals 1 or M represents magnesium and n equals 2.

2. A desensitised peroxygen composition having decreased impact sensitivity comprising not more than 70% w/w potassium 4-sulphoperbenzoic acid, hereinafter KSPB or 50% w/w magnesium 4-sulphoperbenzoic acid, hereinafter MSPB, each according to claim 1, and the balance being a solid diluent in intimate contact with the peroxygen compound.

3. A bleach composition having decreased impact sensitivity comprising a buffering agent or pH regulator and KSPB or MSPB, in such relative amounts that a 1% solution of the composition in water has a pH of 7 to 8.5.

4. A washing composition having decreased impact sensitivity comprising a surfactant and, and containing at least 0.5% w/w KSPB and/or MSPB.

5. A washing composition according to claim 4 containing at least 1% surfactant, at least 1% builder, up to 40% processing acid, up to 20% detergent auxiliary agents and 0.5 to 10% KSPB and/or MSPB.

6. A sanitising composition having decreased impact sensitivity comprising up to 70% alkali metal chloride or bromide, up to 40% KSPB or MSPB and up to 50% surfactant and up to 20% builder.

7. A composition according to comprising a compound claim 1 and having decreased impact sensitivity containing from 0.1 to 5% w/w of a complexing agent satisfying the formula:

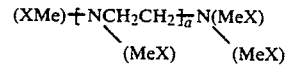

in which X represents a carboxylic acid or a phosphonic acid group or an alkali or alkaline earth metal salt thereof, such as sodium, potassium, calcium or magnesium salt or an ammonium salt and a represents either 0, 1 or 2.

* * * * *